United States Patent
Quon et al.

[11] Patent Number: 6,090,101
[45] Date of Patent: Jul. 18, 2000

[54] METHOD AND APPARATUS FOR PERMANENT HAIR REMOVAL

[76] Inventors: David K. Quon; Hew W. Quon; Wanda A. Quon, all of 808 N. Hill St., Los Angeles, Calif. 90012

[21] Appl. No.: 08/987,956

[22] Filed: Dec. 10, 1997

[51] Int. Cl.[7] .................................................. A61B 17/36
[52] U.S. Cl. .................................................................. 606/9
[58] Field of Search ................................... 606/9, 10, 11, 606/12, 14, 2, 15, 16, 17, 133, 134, 34, 35, 36, 41, 42, 43

[56] References Cited

U.S. PATENT DOCUMENTS

| | | | |
|---|---|---|---|
| 4,484,924 | 11/1984 | Pfleiderer et al. | 8/94.14 |
| 5,011,679 | 4/1991 | Spanier et al. | 424/57 |
| 5,669,916 | 9/1997 | Anderson | 606/133 |

*Primary Examiner*—Linda C.M. Dvorak
*Assistant Examiner*—Sonya C. Harris
*Attorney, Agent, or Firm*—Kleinberg & Lerner, LLP; Marvin H. Kleinberg

[57] ABSTRACT

A permanent hair removal method includes the steps of preparing the surface of the skin, including the removal of excess hair and the application of suitable cleansers and degreasers. Alkaline ions, in a gel, cream, ointment or solution containing a buffered solution of potassium carbonate and sodium bicarbonate are applied to the clean, prepared surface. Apparatus using massage, ultrasound or other treatment modalities, promotes the penetration of the alkaline ions into the skin and hair follicles. The alkaline ions are then heated in situ through the use of a radiant energy source apparatus such as, for example, a laser, a infra red lamp or other high intensity light source. Radiant energy can also be provided by microwave or diathermy sources. The heated alkaline ions will then destroy all hair cells that are encountered.

27 Claims, 3 Drawing Sheets

FIG. 1
PRIOR ART
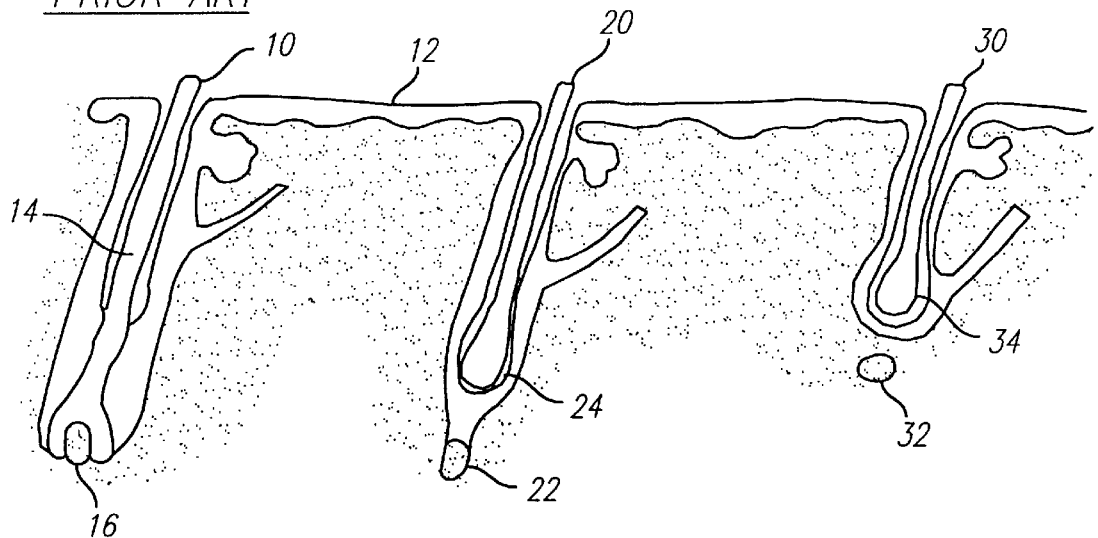
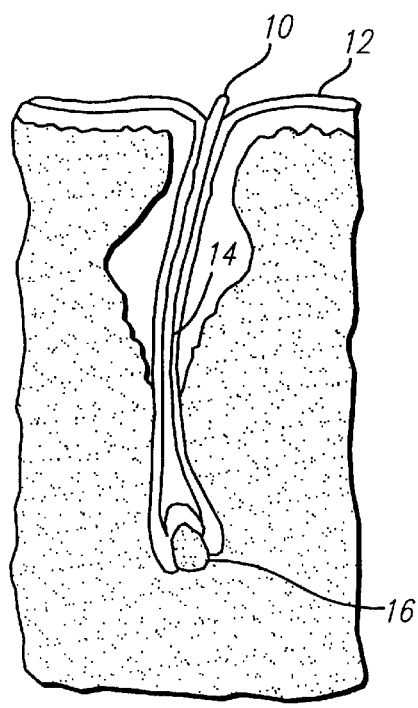
FIG. 2
PRIOR ART
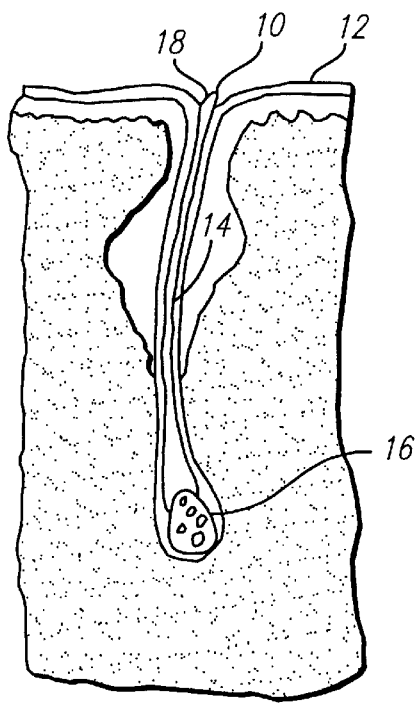
FIG. 3
PRIOR ART

METHOD AND APPARATUS FOR PERMANENT HAIR REMOVAL

BACKGROUND OF THE INVENTION

1. Field of the Invention

The present invention relates to methods for the removal of unwanted human hair and, more particularly, to methods of removing unwanted human hair permanently.

2. Description of the Related Art

There are three cycles in development of the human hair. The first is the resting stage; the second, the growing stage and the third is the shedding stage. In the resting stage, relatively dormant hair cells are present in the epidermis of the skin and are not seen above the skin surface. These hair cells may stay dormant for years. They outnumber the adult or growing hairs by at least 5 to 10 times.

In the growing stage, hair follicles develop downward from the epidermis into the dermal layer. A hair bulb is connected to a small capillary which feeds the hair follicle and its adjacent cellular structures. Research studies have documented that there are many sites in the hair structure which are capable of follicular regeneration. Furthermore, to achieve permanent hair removal, even the sebaceous glands must be destroyed. Therefore, when one simply plucks the hair shaft out, a new hair will grow back in its place.

The currently available hair removal methods include, among others, the traditional electrolysis treatment in which a tiny needle is inserted into the skin down to the hair follicle. Using an electrical direct current, the salt (sodium chloride) ions in the hair follicle are converted into sodium hydroxide which destroys the hair follicle and its adjacent cells. This method is rather painful and carries risks of infection and scarring.

Further, even in the hands of a trained operator, one can never be certain of the accuracy of the placement of the needle tip. This method is very time consuming, requiring about 1 minute to treat each hair. However, when the needle is placed correctly, this method is known to be the most effective one presently available.

The thermolysis method of hair removal is similar to the electrolysis method in that accurate placement of a needle is required for hair destruction. In this case, heat generated in the needle tip causes an inflammatory reaction around the follicle which, in turn, destroys the hair follicle and its adjacent cells.

The thermolysis method is much quicker than the electrolysis method, only requiring 1 to 2 seconds to destroy the hair follicle. It is less effective than electrolysis and requires the accurate placement of a needle.

The blend method is a hybrid of the electrolysis and thermolysis methods. A tiny needle is inserted down to the follicle. Both direct current electrical energy and radio frequency radiant energy are carried down the needle to the site of the follicle. The needle tip conducts a direct current which converts the sodium chloride molecules to sodium hydroxide, as in electrolysis, and the radio frequency components generate heat in the surrounding tissues which causes the inflammatory reaction produced in the thermolysis method. The heat also acts as a catalyst to speed up the destructive process of the alkaline ions. This method is as effective as the electrolysis method and requires 10 to 15 seconds for each hair. However, neither the risks of electrolysis nor thermolysis are reduced.

All of the above described methods work only on hairs in the growing stage and have no effect on hairs in the resting or shedding stages of development.

In the patent to Weissman et al, U.S. Pat. No. 4,388,924, it was proposed that a laser be used to photo-coagulate and therefore devitalize the blood circulation feeding the hair follicles. Where Weissman et al discussed earlier patents that utilized xenon lamps, Weissman et al suggested the use of a laser that could produce a light beam that would penetrate the skin with little or no absorption of energy at the surface, but which would deliver most of the light energy to the hair root.

Weissman et al proposed an argon laser, operating between 480 and 520 nm which would be highly absorbed in the hair root causing coagulation of the blood vessels in the area. However, the method required selective aiming at individual hairs and a complex treatment apparatus was described.

In the patent to Zaias, U.S. Pat. No. 5,059,192, it was suggested that a Q-switched ruby laser, operating at a wavelength of 694 nm, would be absorbed by the melanin concentration at the base of the hair follicle. The absorption of the laser energy by the melanin would cause photothermolysis and melanasomal disruption, including vaporization of the melanin in the follicle.

Other direct effects included vacuolation, edema, gas bubbles and protein denaturation, seriously injuring the follicle and the hair cells in the earlier stages of development. If sufficient energy is delivered by the laser, the hair producing cells are effectively destroyed and there is no regrowth.

An apertured plate was recommended so that different parts of the body could be treated. For example, a 3 mm plate would be used with scalp hairs while openings of from 5 to 8 mm would be used with other body parts. The process could be applied to individual hairs or could treat up to 3 or 4 hairs on the body. The recommended exposure dosages ranged from 0.4 $J/cm^2$ to 10.0 $J/cm^2$ with a suggested optimum of 8.0 $J/cm^2$. Pulses in the range of from 30 to 40 nanoseconds duration were recommended.

More recently, the patent to Tankovich, U.S. Pat. No. 5,425,728, suggested that the photothermolytic effects of the lasers could be enhanced by utilizing contaminants with high absorption of the frequencies employed by the source of radiant energy. The contaminants included carbon in a peach oil which, with massage or ultrasound, could be used to force the carbon into the hair ducts. For this contaminant, a $CO_2$ laser was recommended, with pulses of widths between 200 and 275 ns at repetition rates of from 8 to 30 Hz applied to a 1 $cm^2$ spot and delivering from 0.1 Joules to 0.2 Joule per pulse.

An alternative method uses a near infrared laser at about 1,060 nm but with pulses in the range of 25–30 picoseconds. The energy per pulse was from 3–6 mJ and the spot size was from 0.1 to 0.3 $cm^2$. Another alternative utilized a staining technique and matched the laser to the stain selected. Yet another option was the use of a photosensitizer which made the entire hair shaft susceptible to the applied laser.

These most recent laser methods using red and infrared wavelength are much quicker than the earlier treatments in that the laser can act upon a group of hairs in a fraction of a second. Also, the use of the laser is somewhat less painful and has a much lower risk of infection and scarring than any of the methods mentioned above.

However, all of the laser methods rely on the phenomenon of the laser energy being absorbed by the melanin in the hair follicle, or by a dye or other contaminant, all of which generate heat from the absorbed energy and essentially "burn" the follicle. Where the melanin is the primary target, pulse width is very important because if the pulse width is less than the thermal relaxation time of melanin, the thermal reaction will be confined mainly to the melanin. In such a case, insufficient heat will be generated outside of the melanin to destroy the entire hair follicle, let alone the adjacent apigmented cells.

When the pulse width is greater than the thermal relaxation time of the melanin, the hair follicle is destroyed by the heat. However, some of the surrounding apigmented cells will be injured by the heat released by the absorption of the laser energy by the melanin.

However, as flux or fluence and/or the pulse width of the laser is increased, the risks of scarring, and changes in pigment, and skin texture become proportionally increased. These risks can be reduced slightly but not eliminated by methods such as cooling the hand piece and by the use of topically applied heat sinks such as the gels used with EKG or ultrasound procedures.

To achieve permanent hair removal, it is important to damage or destroy the entire hair follicle, the surrounding apigmented cells, the mid shaft and the sebaceous glands.

SUMMARY OF THE INVENTION

The use of thermolytic methods to remove hair permanently requires that the thermal energy that can be supplied by a radiant energy source be absorbed by a material at the site of the hair follicle. It has been discovered that chemical destruction of the hair follicle, which previously required a hair by hair needle treatment can also be achieved without the use of a needle with a novel and improved method of hair removal that includes two treating steps. In a first step, alkaline ions are introduced into the skin and around the hair follicles.

A second step potentiates the destructive chemical reaction between these alkaline ions and the hair follicles and the structures surrounding the hair follicles, using radiant energy, preferably in the visible region. The effects can be enhanced by the heat created from the effect of the radiant energy on the melanin pigment or from the use of microwave or diathermy to induce local heating.

Because alkaline ions can destroy both the hair follicle and the adjacent apigmented cells, follicular regeneration and hair regrowth can thus be prevented. Further, using a laser as the radiant energy source, less laser energy (fluence and/or pulse width) is needed, thereby reducing the risks normally associated with the use of the laser treatment alone.

The present invention can be used with any hair color while current laser methods generally require dark hair on a light colored skin. Moreover, the alkaline ions used in the present invention can damage and destroy hair cells, even in the absence of melanin.

The method of the present invention offers a more permanent hair removal result than currently available laser removal method because the present method more closely resembles the "blend method" of electrolysis, described above. However the present method is much safer since needle insertion is no longer required. Moreover, the present method is less time consuming because a group of hairs can be treated together. Both the blend method and the present invention employ heat but not as the primary cause of follicle destruction but rather to potentiate the action of alkaline ions which are the principal cause of hair cell destruction.

Because the method of the present invention introduces alkaline ions down into the skin layers, it also causes damage to hair cells which are in the resting stage in the epidermis. These cells are not seen above the skin, and, as a result, they can not be treated by electrolysis, thermolysis or the blend treatment. Moreover, these hair cells are not damaged by currently available laser methods because these cells have little or no melanin, which was the primary target for the laser energy.

The novel features which are characteristic of the invention, both as to structure and method of operation thereof will be understood from the following description, considered in connection with the accompanying drawings, in which the preferred embodiment of the invention is illustrated by way of example. It is to be expressly understood however, that the drawings are for the purpose of illustration and description only, and they are not intended as a definition of the limits of the invention.

FIG. 1 is a cross sectional view of three hair shafts showing the stages of the hair cycle;

FIG. 2 is a cross sectional view of a hair follicle after the hair above the skin surface has been cut;

FIG. 3 is a cross sectional view of the hair follicle of FIG. 2 after treatment;

DESCRIPTION OF THE PREFERRED EMBODIMENTS

Figure 4:
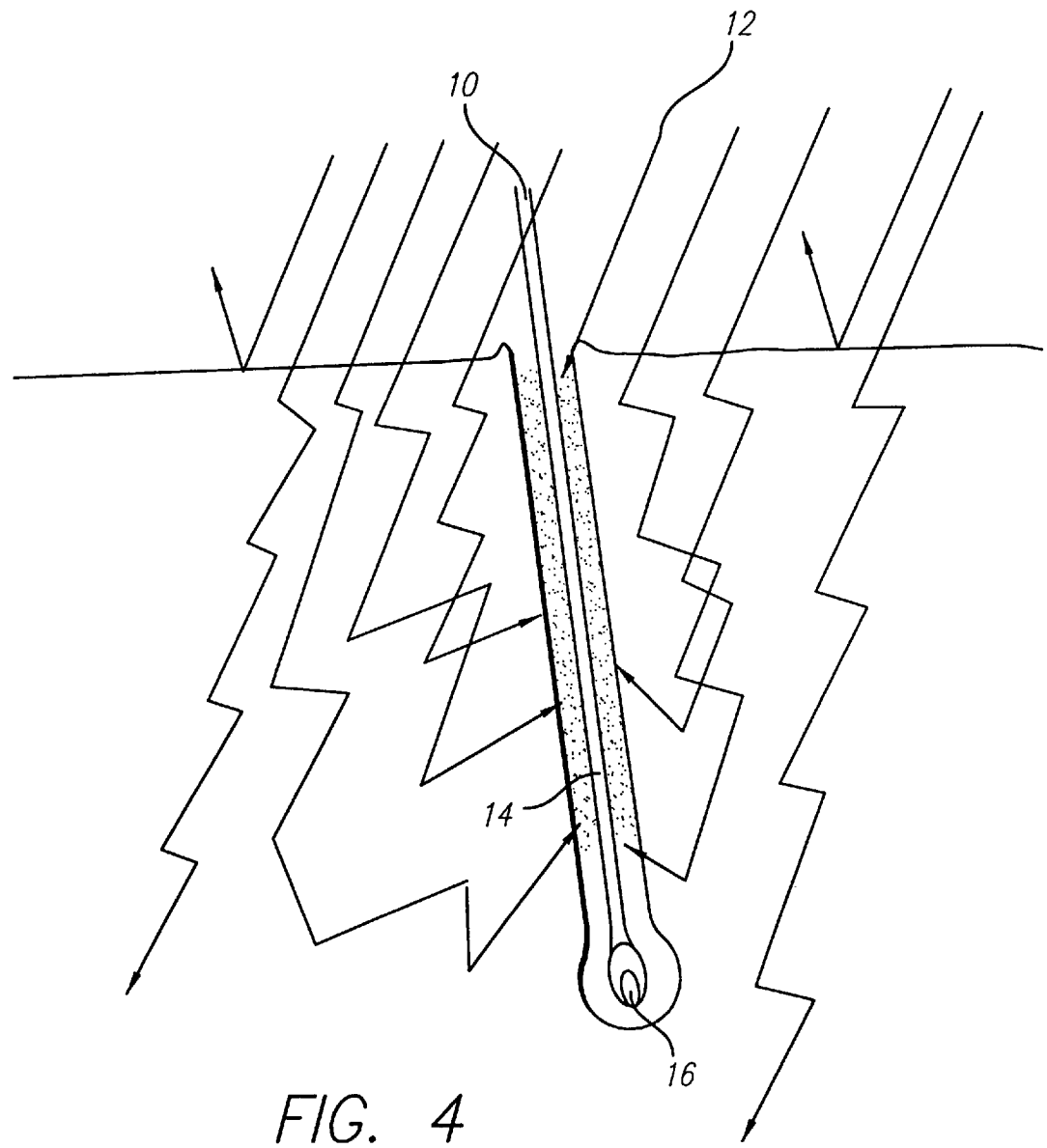
FIG. 4 is a cross sectional view showing the path of photons from a radiant energy source.

In practicing the method of the present inventor, it is desirable that, as a preliminary step, as much the hair as possible be waxed or tweezed out. Alternatively, the hair can be shaved. The skin is cleaned with a degreasing agent.

An alkaline substance, preferably in a form buffered at a pH of 11, such as potassium carbonate and bicarbonate of soda (sodium bicarbonate) is applied in a cream, ointment, gel or solution, to the skin. An optional thin, transparent occlusive dressing can be applied.

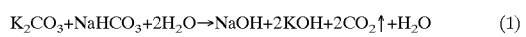

$$K_2CO_3 + NaHCO_3 + 2H_2O \rightarrow NaOH + 2KOH + 2CO_2\uparrow + H_2O \quad (1)$$

Formula (1) defines the reaction that produces the alkaline ions necessary to the practice of the invention. The alkalinity of the ions should be less than a pH of 13 and the range of 10.5–13 is preferred. Any greater alkalinity can cause scarring or other undesired side effects.

The alkaline ions can be transported into the skin using a 12 to 100 volt direct current of approximately 1–20 milliamps. For example, one electrode can be placed in contact with the subject at a place remote from the area to be treated and the second electrode is applied to the area to be treated. The current causes a migration of the alkaline ions through the skin toward the interior near the follicle and other cell sites.

Mechanical means can also be employed to transport the alkaline ions closer to the follicle sites. Gentle manual massage or mechanical massagers may also be used. Ultrasound, or even chemical enhancers such as solvents and penetrants will also act to deliver the ions to the desired place for treatment.

With the alkaline ions in place, the second step activates these alkaline ions. In a preferred embodiment, a laser, preferably with a wavelength within the red and infra-red spectrum (i.e. 600–1200 nm) including, but not limited to the ruby (694.3 nm), alexandrite (755 nm), diode (810 nm) and ND:YAG (1064 nm) can be used. The laser is operated in either the pulsed mode or in the continuous-wave mode. However, a mechanical shutter or interrupter may be employed if continuous mode lasers are used.

The goal is to use the heat, released when the follicle absorbs laser energy, as a catalyst for the alkaline ions to destroy the hair structures, including the adjacent apigmented cells. To the extent that the thermal energy compromises the follicle and the other hair structures comes as a serendipitous, but not unintended, side effect.

The following examples of lasers and their operating parameters are deemed suitable for use in the method of the present invention. Any of the above lasers, if operated in the pulsed mode, can deliver approximately 0.3–150 millisecond pulses with 5.0–100 joules per $cm^2$. The beam spot can range from 2–50 mm in diameter.

Using non-coherent light incorporating wavelengths of from 600–1200 nm in the process, a flux or fluence of around 5–100 joules/$cm^2$ and an exposure duration of 0.3–150 milliseconds should be desired. Similar effects can be achieved using other radiant energy devices such as ultrasound, microwave, diathermy and heat lamps, all of which are capable of producing heat within the skin or tissue.

The current invention for permanent hair removal can be favorably compared to the blend method of electrolysis. In the present invention, alkaline ions are first introduced into the skin and these alkaline ions effect damage to the hair follicles and the adjacent structures using an appropriate source of radiant energy to heat the ions.

The radiant energy may further compromise the hair structure as a result of the absorption of the radiant energy by the hair shaft, follicle or other hair cell.

It is believed that the apparatus to practice the methods disclosed herein is known and the drawings and descriptions of appropriate radiant energy sources and the hair follicles and surrounding tissue are found in, for example the patent to Zaias, Pat. No. 5,059,192 and Tankovich, Pat. No. 5,425,728, which drawings and descriptions are hereby incorporated by reference thereto as though fully repeated herein.

FIG. 1 shows a hair shaft 10 which has been cut down to near the surface of the skin 12. The shaft 10 extends down to the follicle 14 which at the anagen stage of the hair cycle joins the papilla 16. Destruction of the papilla 16 is necessary to prevent hair regrowth. After growing for about three years in the anagen stage, the hair shaft 10 enters the catagen stage represented by hair shaft 20 wherein the papilla 22 separates from the base of the follicle 24. The catagen stage lasts only a few weeks.

Hair shaft 30 represents the telogen stage of the hair cycle wherein the papilla 32 completely separates from the follicle 34 and forms a new secondary hair germ which will repeat the cycle. The telogen stage lasts about three months.

FIG. 2 shows an enlarged view of the hair shaft 10 prior to treatment, wherein the follicle 14 and papilla 16 are normal in appearance in the anagen stage.

FIG. 3 shows the resulting effect on the papilla 16 after treatment according to a preferred embodiment of the method of the present invention. The heated alkaline ions seriously injure the hair follicle and papilla, and destroy the hair germ which would otherwise cause hair regrowth.

Turning next the FIG. 4, there is shown, in idealized cross section, the effect of radiant energy upon the alkaline ions that have been transported from the surface of the skin to the vicinity of the follicle 14 and papilla 16. As the radiant energy beams 40 impinge upon the surface, sufficient heat energy penetrates through the surface of the skin to heat and energize the alkaline ions which then destructively react with the papilla and other hair growing cells.

Figure 5:
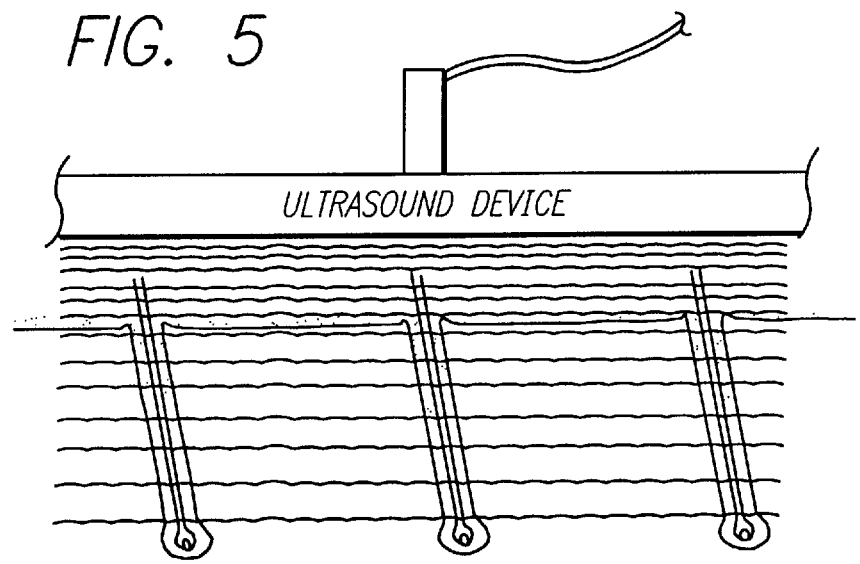
FIG. 5 illustrates the use of an ultrasound device to introduce alkaline ions into the tissues surrounding the hair follicle.

In FIG. 5, there is shown an ultrasound generator of a type useful in causing penetration of the alkaline ions to the subcutaneous area in the vicinity of the follicle 14 and papilla 16.

Figure 6:
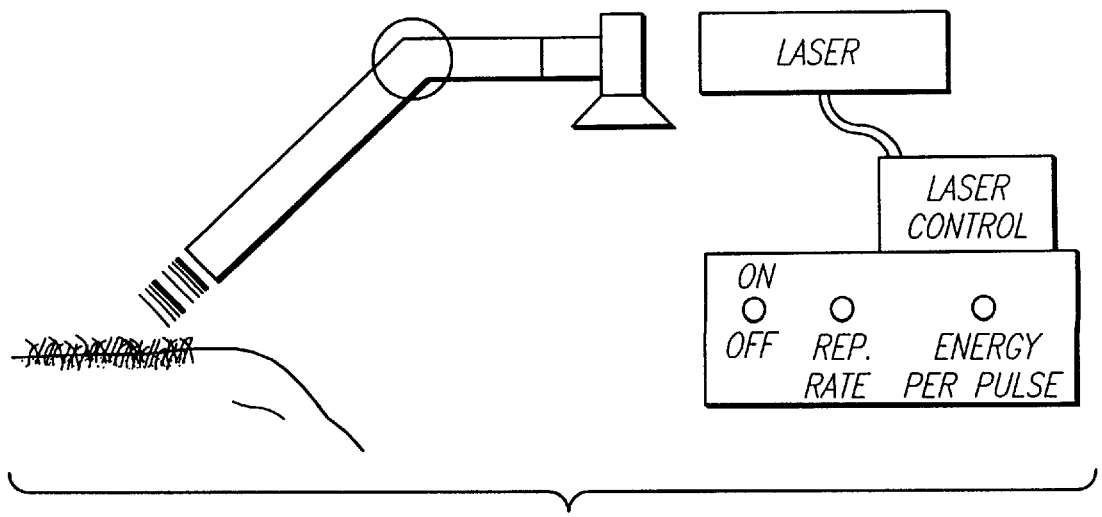
FIG. 6 illustrates the use of a laser and its associated controls useful in heating the alkaline ions.

Finally, in FIG. 6, there is shown a laser device with its associated controls that is a suitable source of radiant energy for heating the alkaline ions in the vicinity of the unwanted hair cells.

FIG. 1 shows a hair shaft 10 which has been cut down to near the surface of the skin 12. The shaft 10 extends down to the follicle 14 which at the anagen stage of the hair cycle joins the papilla 16. Destruction of the papilla 16 is necessary to prevent hair regrowth. After growing for about three years in the anagen stage, the hair shaft 10 enters the catagen stage represented by hair shaft 20 wherein the papilla 22 separates from the base of the follicle 24. The catagen stage lasts only a few weeks Hair shaft 30 represents the telogen stage of the hair cycle wherein the papilla 32 completely separates from the follicle 34 and forms a new secondary hair germ which will repeat the cycle. The telogen stage lasts about three months.

FIG. 2 shows an enlarged view of the hair shaft 10 prior to treatment, wherein the follicle 14 and papilla 16 are normal in appearance in the anagen stage.

FIG. 3 shows the resulting effect on the papilla 16 after treatment according to a preferred embodiment of the method of the present invention. The heated alkaline ions seriously injure the hair follicle and papilla, and destroy the hair germ which would otherwise cause hair regrowth.

Turning next the FIG. 4, there is shown, in idealized cross section, the effect of radiant energy upon the alkaline ions that have been transported from the surface of the skin to the vicinity of the follicle 14 and papilla 16. As the radiant energy beams 40 impinge upon the surface, sufficient heat energy penetrates through the surface of the skin to heat and energize the alkaline ions which then destructively react with the papilla and other hair growing cells.

In FIG. 5, there is shown an ultrasound generator of a type useful in causing penetration of the alkaline ions to the subcutaneous area in the vicinity of the follicle 14 and papilla 16.

Finally, in FIG. 6, there is shown a laser device with its associated controls that is a suitable source of radiant energy for heating the alkaline ions in the vicinity of the unwanted hair cells.

Although the present invention has been described in considerable detail with reference to certain preferred versions and uses thereof, other versions and uses are possible and the scope of the invention should be limited only by the breadth of the claims appended hereto.

What is claimed as new is:

1. Method for permanent hair removal from living human skin having unwanted growing hair by destroying undesired hair cells comprising the steps of:
   a) introducing a compound containing alkaline ions into the skin surface in the region of undesired hair; and
   b) heating said alkaline ions with radiant energy providing at least 1.0 joule /$cm^2$,
   whereby said alkaline ions attack and destroy hair cells in various stages of growth.

2. The process of claim 1 wherein the introducing step further includes the steps of:
   a. removing surface hair; and b. cleaning and degreasing the skin surface.

3. The process of claim 1 wherein said introducing step compound contains potassium carbonate.

4. The process of claim 1, wherein said introducing step compound contains sodium bicarbonate.

5. The process of claim 1, wherein said alkali ions are transported to the site of the hair cells to be destroyed by massaging the skin to which said alkali ions have been applied.

6. The process of claim 1, wherein said alkali ions are transported to the site of the hair cells to be destroyed by using ultrasound on the skin to which said alkali ions have been applied.

7. The process of claim 1, wherein said alkali ions are transported to the site of the hair cells to be destroyed by adding a chemical penetrant on the skin to which said alkali ions have been applied.

8. The process of claim 1, wherein said alkali ions are transported to the site of the hair cells to be destroyed by a direct current electrical potential between the skin to which said alkali ions have been applied and the structure below the skin.

9. The process of claim 1, wherein the heating step includes irradiating the area of interest with a laser operating in the red to infrared region with a wavelength ranging from 650 to 1200 nm.

10. The process of claim 9, wherein the laser is operated in an interrupted mode with irradiation applied in exposure intervals ranging a duration of from 0.3 to 150 ms at a power ranging from 5–100 joules/cm$^2$.

11. The process of claim 1, wherein the heating step includes irradiating the area of interest with a non-coherent radiant energy source providing from 5–100 joules/cm$^2$ in pulses having a duration ranging from 0.3 to 150 ms.

12. The process of claim 1, wherein the heating step includes irradiating the area of interest with a source of microwave energy.

13. The process of claim 1, wherein the heating step includes irradiating the area of interest with diathermy.

14. Method for permanent hair removal from living human skin having unwanted growing hair by destroying undesired hair cells comprising the steps of:

a) removing surface hair;

b) cleaning and degreasing the skin surface;

c) introducing a compound containing alkaline ions into the skin surface in the region of undesired hair;

d) massaging the skin to which said alkali ions have been applied; and e) heating said alkaline ions by irradiating the area of interest with a laser operating in the red to infrared region with a wavelength ranging from 600 to 1200 nm operating to apply radiant energy of at least 5 joules/cm$^2$, whereby said alkaline ions attack and destroy hair cells in various stages of growth.

15. The process of claim 14 wherein said introducing step compound includes potassium carbonate to provide alkaline ions.

16. The process of claim 14, wherein said introducing step compound includes sodium bicarbonate to provide alkaline ions.

17. Method for permanent hair removal from living human skin having unwanted growing hair by destroying undesired hair cells comprising the steps of:

a) removing surface hair;

b) cleaning and degreasing the akin surface;

c) introducing a compound containing alkaline ions into the skin surface in the region of undesired hair;

d) transporting said alkali ions below the surface of the skin to which said ions have been applied; and e) heating said alkaline ions by irradiating the area of interest with non-coherent radiant energy ranging from 5–100 joules/cm$^2$ in pulses having a duration ranging from 0.3 to 150 milliseconds, whereby said alkaline ions attack and destroy hair cells in various stages of growth.

18. Apparatus for permanently removing hair from living human skin having unwanted growing hair by destroying undesired hair cells comprising the combination of:

a. ion introducing means for transporting alkaline ions from the skin surface to undesired hair cells beneath the skin surface; and b. heating means for heating and activating alkaline ions below the skin surface to interact with and destroy unwanted hair cells.

19. Apparatus for removing hair as in claim 18, wherein said ion introducing means include a first electrode applied to a human body having unwanted hair cells, a second electrode at the site of ion transport and direct current supply means capable of applying D.C. currents ranging from 1–20 milliamperes at voltages ranging from 12–100 volts whereby the current through the body effectively moves alkaline ions below the skin into the tissues of the body adjacent unwanted hair cells.

20. Apparatus for removing hair as in claim 18, wherein said ion introducing means include an ultrasound generator for applying ultrasonic waves to the skin surface in the vicinity of unwanted hair cells, whereby the ultrasonic waves cause the alkaline ions to be transported below the surface of the skin.

21. Apparatus for removing hair as in claim 18, wherein said ion introducing means include a mechanical vibrating massager for facilitating the transport of alkaline ions beneath the surface of the skin.

22. Apparatus for removing hair as in claim 18, wherein said heating means include a pulsed laser operating in the range between 600 and 1200 nm with energy in the range ranging 5–100 joules/cm$^2$, a pulse duration of from 0.3–150 milliseconds and an illumination spot size ranging from 2–50 mm.

23. Apparatus for removing hair as in claim 22, wherein said pulsed laser is selected from a group consisting of ruby laser (694.3 nm), alexandrite laser (720–780 nm), diode laser (600–1100 nm) and neodymium-yag laser (1064 nm).

24. Apparatus for removing hair as in claim 18, wherein said heating means include a continuous wave laser operating in the range between 600 and 1200 nm with energy in the range between 1 and 500 watts/cm$^2$ and an illumination spot size ranging from 1–50 mm.

25. Apparatus for removing hair as in claim 24, wherein said continuous wave laser is selected from a group consisting of ruby laser (694.3 nm), alexandrite laser (720–780 nm), diode laser (600–1100 nm) and neodymium-yag laser (1064 nm).

26. The apparatus for removing hair as in claim 18, wherein said alkaline ions are derived from mixture at a pH ranging from 8–13 selected from the group consisting of potassium and sodium carbonates and bicarbonates present in a medium selected from the group consisting of solutions, pastes, creams, gels, ointments and lotions.

27. The apparatus for removing hair as in claim 26 wherein said alkaline ions are buffered to a pH of 11.

* * * * *